(12) United States Patent
Sylvestre et al.

(10) Patent No.: US 11,769,264 B2
(45) Date of Patent: *Sep. 26, 2023

(54) METHOD AND SYSTEM FOR IMAGING A BIOLOGICAL TISSUE

(71) Applicant: OPTINA DIAGNOSTICS, INC., Montreal (CA)

(72) Inventors: Jean Philippe Sylvestre, Kirkland (CA); David Lapointe, Pointe-Claire (CA); Claudia Chevrefils, Saint-Laurent (CA); Reza Jafari, Beaconsfield (CA)

(73) Assignee: OPTINA DIAGNOSTICS INC., Montreal (CA)

( * ) Notice: Subject to any disclaimer, the term of this patent is extended or adjusted under 35 U.S.C. 154(b) by 44 days.

This patent is subject to a terminal disclaimer.

(21) Appl. No.: 17/201,259

(22) Filed: Mar. 15, 2021

(65) Prior Publication Data

US 2021/0201514 A1 Jul. 1, 2021

Related U.S. Application Data

(62) Division of application No. 16/340,612, filed as application No. PCT/IB2017/056509 on Oct. 19, 2017, now Pat. No. 10,964,036.

(Continued)

(51) Int. Cl.
*G06T 7/40* (2017.01)
*G06T 7/00* (2017.01)
(Continued)

(52) U.S. Cl.
CPC .............. *G06T 7/40* (2013.01); *G01N 21/25* (2013.01); *G06T 3/0068* (2013.01);
(Continued)

(58) Field of Classification Search
CPC .... G06T 7/40; G06T 7/77; G06T 7/97; G06T 3/0068; G06T 7/0012; G06T 2207/10152; G06T 2207/30024
See application file for complete search history.

(56) References Cited

U.S. PATENT DOCUMENTS

| 6,081,612 A | 6/2000 | Gutkowitcz-Krusin et al. |
| 6,208,749 B1 | 3/2001 | Gutkowitcz-Krusin et al. |

(Continued)

FOREIGN PATENT DOCUMENTS

| CN | 102938148 A | 2/2013 |
| CN | 105046265 A * | 11/2015 |

(Continued)

OTHER PUBLICATIONS

Mahlein, A. K., Steiner, U., Hillnhutter, C., Dehne, H. W., & Oerke, E. C. (2012). Hyperspectral imaging for small-scale analysis of symptoms caused by different sugar beet diseases. Plant methods, 8(1), 3. https://doi.org/10.1186/1746-4811-8-3 (Year: 2012).*

(Continued)

*Primary Examiner* — Ian L Lemieux
(74) *Attorney, Agent, or Firm* — BCF LLP (57) ABSTRACT

The present disclosure relates to a method and a system for imaging a biological tissue. A monochromatic image of the biological tissue is obtained. A texture analysis of the biological tissue is performed using spatial information of the monochromatic image to identify features of the biological tissue. A texture image is generated based on the features of the biological tissue. The biological tissue of the subject is classified as normal or abnormal at least in part based on a comparison between first order statistics of the texture image and predetermined values.

12 Claims, 10 Drawing Sheets

Related U.S. Application Data (60) Provisional application No. 62/410,552, filed on Oct. 20, 2016.

(51) Int. Cl.
| | | |
|---|---|---|
| *G01N 21/25* | (2006.01) | |
| *G06T 3/00* | (2006.01) | |
| *G06T 7/77* | (2017.01) | |
| *A61B 3/12* | (2006.01) | |
| *A61B 5/02* | (2006.01) | |
| *A61B 5/00* | (2006.01) | |
| *G01N 21/55* | (2014.01) | |
| *G01N 21/64* | (2006.01) | |

(52) U.S. Cl.
CPC ............. *G06T 7/0012* (2013.01); *G06T 7/77* (2017.01); *G06T 7/97* (2017.01); *A61B 3/12* (2013.01); *A61B 5/02007* (2013.01); *A61B 5/4088* (2013.01); *A61B 5/4381* (2013.01); *A61B 5/444* (2013.01); *G01N 21/55* (2013.01); *G01N 21/6456* (2013.01); *G06T 2207/10152* (2013.01); *G06T 2207/30024* (2013.01)

(56) References Cited

U.S. PATENT DOCUMENTS

| | | | |
|---|---|---|---|
| 6,587,575 | B1 | 7/2003 | Windham et al. |
| 7,187,810 | B2 | 3/2007 | Clune et al. |
| 7,562,057 | B2 | 7/2009 | Maggioni |
| 7,751,594 | B2 | 7/2010 | Rowe et al. |
| 8,280,134 | B2 | 10/2012 | Hoyt |
| 8,787,638 | B2 | 7/2014 | Zee et al. |
| 9,808,155 | B2 | 11/2017 | Verdooner |
| 10,004,403 | B2 | 6/2018 | Debernardis et al. |
| 2003/0095721 | A1 | 5/2003 | Clune et al. |
| 2004/0207625 | A1 | 10/2004 | Griffin et al. |
| 2006/0062438 | A1 | 3/2006 | Rowe |
| 2006/0245631 | A1 | 11/2006 | Levenson et al. |
| 2006/0274921 | A1 | 12/2006 | Rowe |
| 2007/0140540 | A1 | 6/2007 | McLaren et al. |
| 2007/0263915 | A1 | 11/2007 | Mashiach |
| 2008/0232534 | A1 | 9/2008 | Rowe |
| 2010/0208951 | A1* | 8/2010 | Williams ............. G06V 10/143 382/117 |
| 2011/0026804 | A1* | 2/2011 | Jahanbin ............... G06T 7/0004 382/141 |
| 2011/0242306 | A1 | 10/2011 | Bressler et al. |
| 2012/0008838 | A1 | 1/2012 | Guyon et al. |
| 2012/0314920 | A1 | 12/2012 | Prigent et al. |
| 2014/0140629 | A1* | 5/2014 | Tai ......................... G06T 7/0012 382/218 |
| 2014/0348750 | A1 | 11/2014 | Vince et al. |
| 2017/0076442 | A1 | 3/2017 | Schoenmeyer et al. |
| 2017/0169276 | A1* | 6/2017 | Agaian ................ A61B 5/4381 |
| 2018/0078134 | A1* | 3/2018 | Katz .................... A61B 3/0025 |
| 2020/0015734 | A1 | 1/2020 | Mayer |
| 2022/0240779 | A1* | 8/2022 | Peyman ............... A61B 5/4088 |

FOREIGN PATENT DOCUMENTS

| | | | |
|---|---|---|---|
| JP | H01242941 | A | 9/1989 |
| JP | 2003144412 | A | 5/2003 |
| JP | 2008541048 | A | 11/2008 |
| JP | 2012143349 | A | 8/2012 |
| JP | 2014029287 | A | 2/2014 |
| JP | 2016519321 | A | 6/2016 |
| JP | 2016154810 | A | 9/2016 |
| JP | 2016504563 | A5 | 1/2018 |
| WO | 2003098522 | A1 | 11/2003 |
| WO | 2010063010 | A2 | 6/2010 |
| WO | 2014076789 | A1 | 5/2014 |
| WO | 2016041062 | A1 | 3/2016 |
| WO | 2016075096 | A1 | 5/2016 |

OTHER PUBLICATIONS

Selvathi et al., Automated Detection of Diabetic Retonopathy for Early Diagnosis using Feature Extraction and Support Vector Machine, International Journal of Emerging Technology and Advanced Engineering, vol. 2, Issue 11, Nov. 2012, pp. 103-108.

Tesar et al., Medical image anlysis of 3D CT images based on extension of Haralick texture features, Computerized Medical Imagining and Graphics, vol. 32, 2008, pp. 513-520.

Rathore et al., A Recent Survey on Colon Cancer Detection Techniques, IEEE/ACM Transactions on Computational Biology and Bioinfomnatics, vol. 10, No. 3, May/Jun. 2013, pp. 545-563.

Esgiar et al., Microscopic Image Analysis for Quantitative Measurement and Feature Identification of Normal and Cancerous Colonic Mucosa, IEEE Transactions on Information Technology in Biomedicine, vol. 2, No. 3, Sep. 1998, pp. 197-203.

Khelifi et al., Multispectral texture characterization: application to computer aided diagnosis on prostatic tissue mages, EURASIP Journal on Advances in Signal Processing, pp. 1-13, 2012, vol. 2012:118.

ISA/CA, International Search Report of PCT/IB2017/056509, Anthony Glaser, dated Jan. 24, 2018.

English translation of CN102938148A retrieved from https://worldwide.espacenet.com/ on Apr. 9, 2019.

Aggarwal et al., First and Second Order Statistics Features for Classification of Magnetic Resonance Brain Images, Journal of Signal and Information Processing, 2012, 3, pp. 146-153, Published Online May 2012 (http://www.SciRP.org/journal/jsip).

Huang et al., A Multichannel Gray Level Co-Occurrence Matrix for Multi/Hyperspeclial Image Texture Representation, Remote Sens. 2014, 6, pp. 8424-8445; ISSN 2072-4292, www.mdpi.com/journal/remotesensing.

Xu et al., Hyperspectral Image Denoising Using a Spatial—Spectral Monte Carlo Sampling Approach, IEEE Journal of Selected Topics in Applied Earth Observations and Remote Sensing , 2015.

Xie et al. , Spectrum and Image Texture Features Analysis for Early Blight Disease Detection on Eggplant Leaves, Sensors, pp. 1-15, 2016, 16, 676, www.mdpi.com/journal/sensors.

Giraddi et al., "Abnormality Detection in retinal images using Haar wavelet and First order features", 2016, 2nd International Conference on Applied and Theoretical Computing and Communication Technology (iCATccT), pp. 657-661.

Sabeenian et al., "Texture-based medical image classification of computed tomography images using MRCSF", International Journal of Medical Engineering and Informatics, 2009, vol. 1, No. 4, pp. 459-472.

Su et al., "Hyperspectral image classification based on volumetric texture and dimensionality reduction", Front. Earth Sci., 2015, vol. 9, No. 2, pp. 225-236.

European Search Report dated Apr. 17, 2020 from the EPO in connection with the corresponding application No. 17863230.3.

English translation of JP2016154810A retrieved form https://patents.google.com/patent/JP2016154810A/en?oq=JP2016154810 on Jul. 21, 2021.

English translation of JP2008541048A retrieved form https://patents.google.com/patent/JP2008541048A/en?oq=JP2008541048 on Jul. 21, 2021.

English Abstract of JPH01242941A retrieved form https://patents.google.com/patent/JPH01242941A/en?oq=JP1242941 on Jul. 21, 2021.

English translation of JP2003144412A retrieved form https://patents.google.com/patent/JP2003144412A/en?oq-JP2003144412 on Jul. 21, 2021.

English translation of JP2012143349A retrieved form https://patents.google.com/patent/JP2012143349A/en?oq=JP2012143349 on Jul. 21, 2021.

English translation of JP2014029287A retrieved form https://patents.google.com/patent/JP2014029287A/en?oq=JP2014029287 on Jul. 21, 2021.

English translation of JP2016504563A retrieved form https://patents.google.com/patent/JP2016504563A/en?oq=JP2016504563 on Jul. 21, 2021.

(56) References Cited

OTHER PUBLICATIONS

English translation of WO2014076789A1 retrieved form https://patents.google.com/patent/WO2014076789A1/en?oq=WO2014076789 on Jul. 21, 2021.
English translation of JP2016519321A retrieved form https://patents.google.com/patent/JP2016519321A/en?oq=JP2016519321 on Jul. 21, 2021.

* cited by examiner

METHOD AND SYSTEM FOR IMAGING A BIOLOGICAL TISSUE

CROSS-REFERENCE

The present application is a divisional of U.S. patent application Ser. No. 16/340,612, filed on Apr. 9, 2019, which is a National Phase Entry of International Application Serial No. PCT/IB2017/056509, filed on Oct. 19, 2017, which claims priority from U.S. Provisional Patent Application Ser. No. 62/410,552, filed on Oct. 20, 2016, the entirety of all of which is incorporated by reference herein.

TECHNICAL FIELD

The present disclosure relates to the field of medical imaging. More specifically, the present disclosure relates to a method and a system for detecting an anomaly within a biological tissue.

BACKGROUND

Imaging techniques are commonly used to assist in the detection and diagnosis of various illnesses. Images of a particular region of interest (ROI) of a subject are analysed to detect anomalies. A commonly used technique to detect amyloids and other anomalies comprises positron emission tomography (PET) scanning. PET scans are expensive, time consuming, and may cause discomfort to the subject.

One example of anomalies that may be detected and lead to the establishment of a diagnosis comprises amyloids, that is, abnormal protein aggregates. In particular, while Alzheimer's disease is essentially a neurodegenerative illness, it has been shown that the presence of amyloid plaques in the retina of a subject may indicate the onset of Alzheimer's disease. It has further been proposed to the diagnosis of other illnesses, for example diabetes and hypertension, could be based on the detection of anomalies within the retina of a subject.

Recently, techniques involving numerical image processing have been proposed. In particular, image analysis may be used to characterize image textures with the aim of discovery abnormal patterns within a ROI of the subject. Currently, there are few commercially available technologies capable of efficiently detecting, within the eye of a subject, a manifestation of a disease rooted in other organs of the subject. An example of such technology may be found in International Patent Application Publication No. WO 2016/041062 A1 to Sylvestre et al., published on Mar. 23, 2016, the disclosure of which is incorporated by reference herein in its entirety, which discloses techniques for producing spectrally resolved images that may be used for identifying amyloid plaques present in the fundus of a subject suffering from the onset of Alzheimer's disease.

Figure 1:
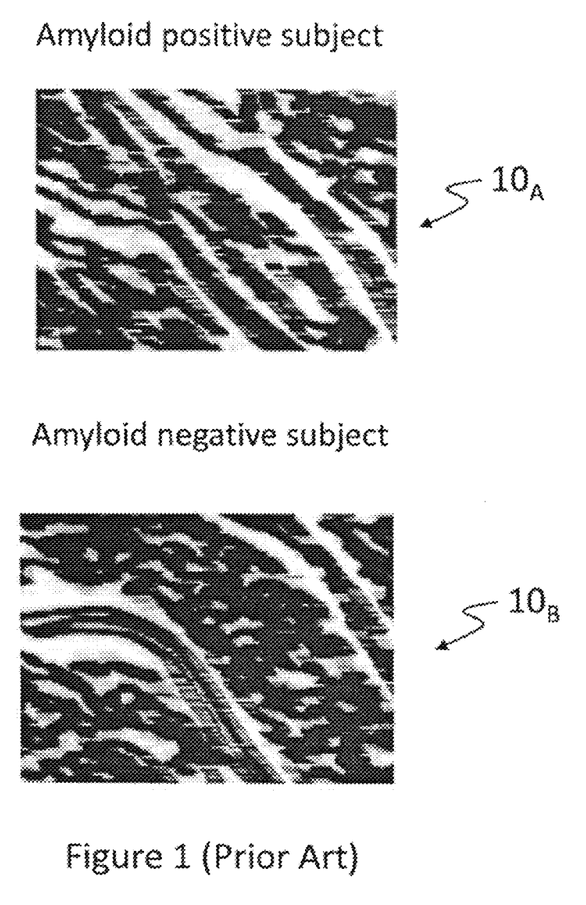
FIG. 1 (prior art) is a representation of texture correlations based on spatial GLCM for regions of interest of two subjects, one of which being amyloid positive.

Gray level co-occurrence matrix (GLCM) analysis has been proposed as a tool for the representation of the texture of a ROI. For instance, FIG. 1 (prior art) is a representation of texture correlations based on spatial GLCM for regions of interest of two subjects, one of which being amyloid positive. In FIG. 1, the ROI is within the retina of the two subjects. Photograph $10_A$ shows a ROI for an amyloid positive subject (hereinafter patient "A") while photograph $10_B$ shows a similar ROI for an amyloid negative subject (hereinafter patient "B"). While photographs $10_A$ and $10_B$ do reveal some differences between these ROIs, these differences are subtle and may not suffice to easily discriminate between normal and abnormal conditions. Diagnosis based on photographs $10_A$ and $10_B$ requires the attention of a highly skilled medical professional. In spite of the skill of the medical professional, diagnosis errors may occur due to the ambiguous distinction between photographs $10_A$ and $10_B$ that respectively show abnormal and normal tissues.

Current imaging techniques tend to provide visual information that can only be evaluated by highly skilled professionals. Moreover, current imaging techniques are generally not easily adaptable to the detection of various types of anomalies in various biological tissues such as ROIs of a subject.

Therefore, there is a need for improvements in the field of medical imaging that compensate for problems related to the limited adaptability of current imaging techniques and to the inherent ambiguity of images obtained using such techniques.

SUMMARY

According to the present disclosure, there is provided a method of detecting an anomaly within a biological tissue. A first image of the biological tissue is obtained, the first image containing light at a first wavelength. A second image of the biological tissue is obtained, the second image containing light at a second wavelength. A texture analysis of the biological tissue is performed using spatial information of the first and second images. The texture analysis is resolved over the first and second wavelengths.

According to the present disclosure, there is also provided a system for detecting an anomaly within a biological tissue. The system comprises a receiver of a first image and of a second image of the biological tissue and a processor operatively connected to the receiver. The processor is configured to perform a texture analysis of the biological tissue using spatial information of the first and second images, the texture analysis being resolved over a first wavelength of the first image and over a second wavelength of the second image.

According to the present disclosure, there is also provided a method of detecting an anomaly within a biological tissue. A monochromatic image of the biological tissue is obtained. A texture analysis of the biological tissue is performed using spatial information of the monochromatic image of the biological tissue to identity features of the biological tissue. A texture image is generated based on the features of the biological tissue. The biological tissue of the subject is classified as normal or abnormal at least in part based on a comparison between first order statistics of the texture image and predetermined values.

The present disclosure further relates to a system for detecting an anomaly within a biological tissue. The system comprises a receiver of a monochromatic image of the biological tissue and a processor operatively connected to the receiver. The processor is configured to perform a texture analysis of the biological tissue using spatial information of the monochromatic image of the biological tissue to identify features of the biological tissue, generate a texture image based on the features of the biological tissue, and classify the biological tissue of the subject as normal or abnormal at least in part based on a comparison between first order statistics of the texture image and predetermined values.

The foregoing and other features will become more apparent upon reading of the following non-restrictive description of illustrative embodiments thereof, given by way of example only with reference to the accompanying drawings.

BRIEF DESCRIPTION OF THE DRAWINGS

Embodiments of the disclosure will be described by way of example only with reference to the accompanying drawings, in which.

Like numerals represent like features on the various drawings.

DETAILED DESCRIPTION

Various aspects of the present disclosure generally address one or more of the problems related to the limited adaptability of current imaging techniques and to the inherent ambiguity of images obtained using such techniques.

Figure 2:
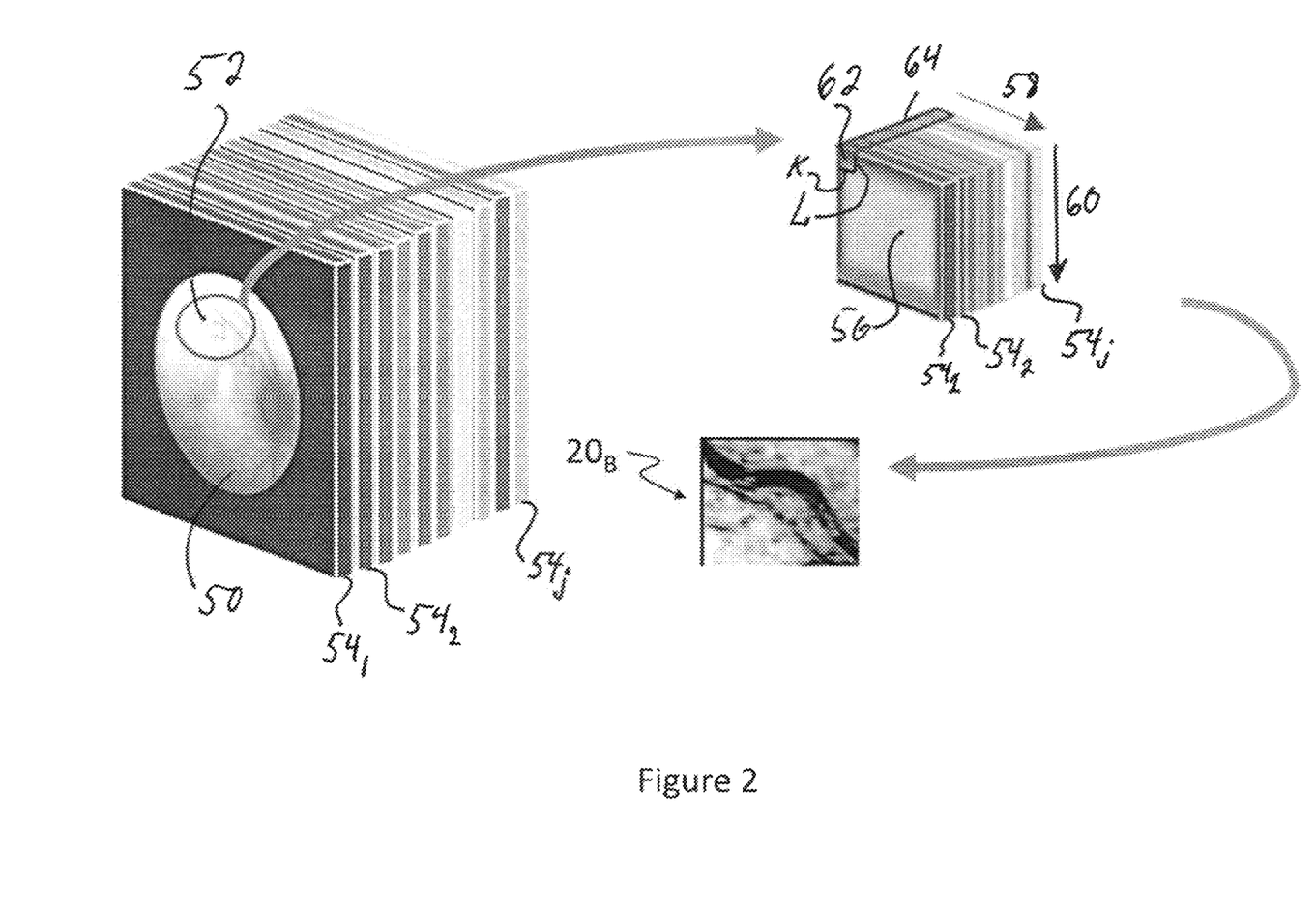
FIG. 2 is a schematic representation of a process for using a moving window to build a texture image of a biological tissue based on spatial and spectral information.

Generally speaking, the present technology adds, to spatial information inherently present in two-dimensional images, a third dimension defined by the use of spectral information. Images of a biological tissue are obtained in two (2) or more wavelengths. Referring now to the drawings, FIG. 2 is a schematic representation of a process for using a moving window to build a texture image, or texture map, of a biological tissue based on spatial and spectral information. On FIG. 2, the biological tissue is found in a region of interest (ROI) of a subject. An organ or tissue 50 of a subject contains a ROI 52 from which a plurality of images $54_1, 54_2 \ldots 54_j$ are obtained at j distinct wavelengths to generate a hyperspectral image 56 of the ROI 52. Each one of the plurality of images $54_1, 54_2 \ldots 54_j$ may be obtained by capturing reflectance or fluorescence emitted from the ROI 52. The images $54_1, 54_2 \ldots 54_j$ as well as the hyperspectral image 56 each contain a plurality of pixel rows 58 and a plurality of pixel columns 60. A portion of the hyperspectral image 56, in a window 62, contains spatial information over a width of k pixels and a height of l pixels, in which each of k and l are greater than or equal to one (1) pixel, this window 62 also containing spectral information 64 defined over the j distinct wavelengths. A texture analysis of the hyperspectral image 56 is performed based on spatial information contained in the k·l pixels of the window 62, the texture analysis being resolved over the j distinct wavelengths. By moving the window 62 over the area of the ROI 52, the texture analysis provides a texture image $20_B$ of the ROI 52. The texture image $20_B$ contains information describing the ROI 52, for example normalised contrast image, normalised homogeneity image, normalised correlation image and/or normalised energy image of the ROI 52.

In the context of the present disclosure, a biological tissue may include a region of interest (ROI) and may be as large as a complete organ or larger, or as small as any tissue or portion thereof sufficient for the eventual detection of an anomaly and/or for the establishment of a diagnostic. In a non-limiting example, the biological tissue may comprise the retina of a subject, or a part thereof, and the anomaly being searched may comprise the presence of amyloid plaques near a blood vessel of the retina. In another non-limiting example, the biological tissue may be obtained from a biopsy performed on the subject. Imaging of the biological tissue may take place in vivo, ex vivo and/or in vitro.

Figure 3:
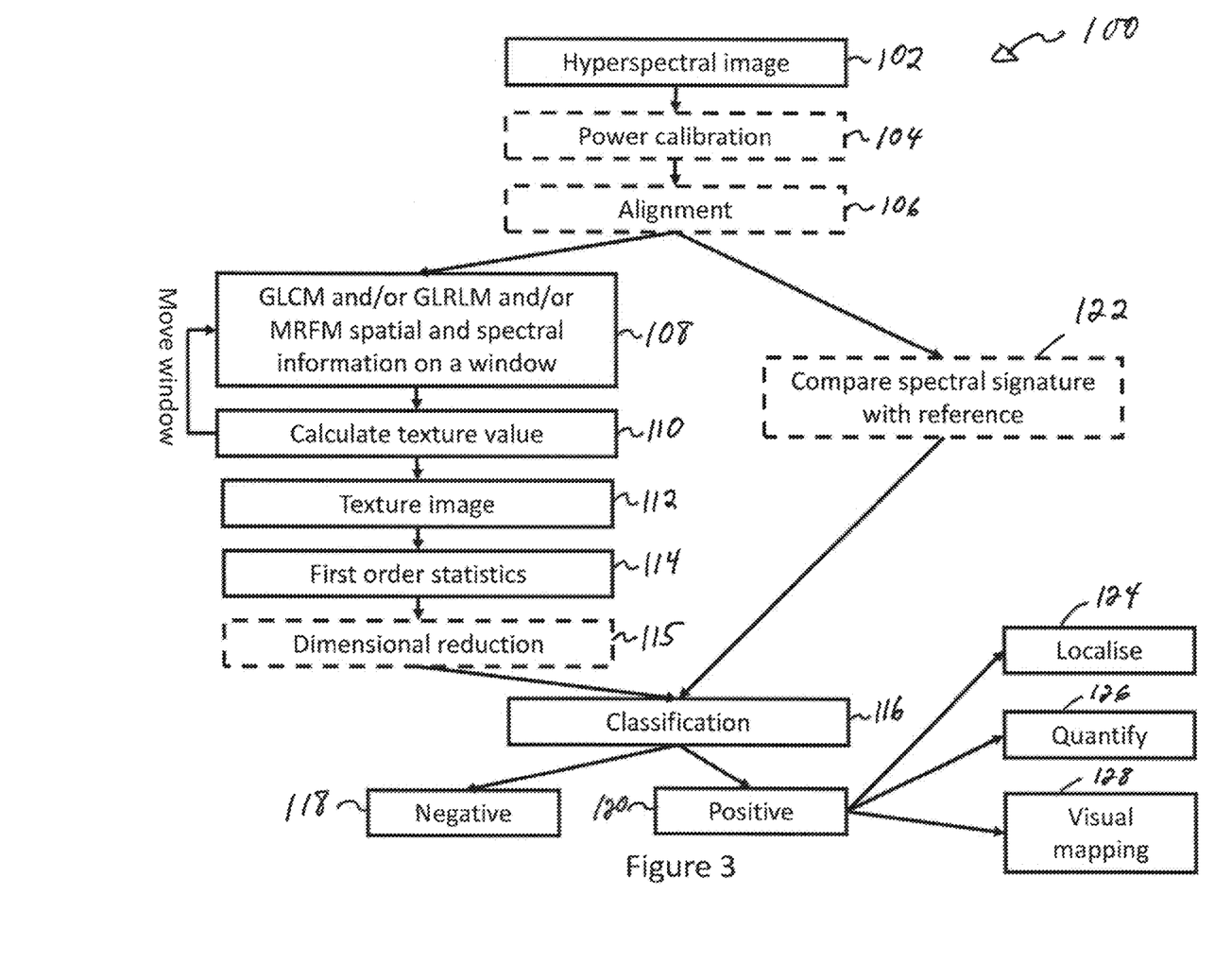
FIG. 3 is a sequence diagram of a process using GLCM and/or GLRLM and/or MRFM in spatial and spectral directions and using texture information to classify images of a biological tissue according to an embodiment.

FIG. 3 is a sequence diagram of a process using GLOM and/or GLRLM and/or MRFM in spatial and spectral directions and using texture information to classify images of a biological tissue according to an embodiment. On FIG. 3, a sequence 100 comprises a plurality of operations that may be executed in variable order, some of the operations possibly being executed concurrently, some of the operations being optional.

A hyperspectral image of the biological tissue is obtained at operation 102. The hyperspectral is composed of a plurality of images of the biological tissue obtained at a plurality of corresponding wavelengths. At a minimum, two (2) images of the biological tissue are obtained at two (2) distinct wavelengths. In one variant, the hyperspectral image may comprise a third image of the biological tissue containing light at a third wavelength. In another variant, the hyperspectral image may comprise a larger number of images, each of these images containing light at a corresponding wavelength. To generate the hyperspectral image, an image acquisition device (not shown), for example a camera, acquires the first and second images as well as any further image. In an embodiment, the first, second and any further images are obtained simultaneously by the image acquisition device. Other image acquisition methods such as, in non-limiting examples, successive acquisition of images at various wavelengths and scanning laser ophthalmology (SLO) imaging are also contemplated.

Light intensities, or luminance, of the first and second images, and of any further image if available, may be calibrated at operation 104 to correct for eventual power variations over distinct wavelengths caused by imaging equipment providing these images. Likewise, when the imaging equipment does not provide consistent alignment of images at each wavelength, alignment registration of the first, second and any further images may be made at operation 106 so that corresponding pixels of these images correspond to a same element of the biological tissue. Operations 104 and 106 are optional and may not be present in embodiments in which imaging equipment provides calibrated and aligned images.

A texture analysis of the biological tissue is performed using spatial information of at least the first and second images, also using spatial information of any further images of the biological tissue if available, the texture analysis being resolved over at least the first and second wavelengths, and over wavelengths of these further images of the biological tissue if available. This texture analysis is performed at operations 108 and 110. For each pixel of the first, second and any further image of the biological tissue, the texture analysis is performed at operation 108 to identify features of the biological tissue by calculating a matrix, for example using gray level co-occurrence matrix (GLOM), a gray level run length matrix (GLRLM), a Markov Random Field Matrix (MRFM), or any combination of GLOM, GLRLM and MRFM applied on spatial and spectral information of the first, second and any further image of the biological tissue. A texture value is calculated at operation 110. Operations 108 and 110 are repeated over pixel rows and pixel columns of the first and second images and of any further image.

In a non-limiting embodiment, the texture image is generated at operation 112, based on the features of the biological tissue identified in the texture analysis of the first, second, and any further images. A set of biological tissue images, including the first, second and any further images of the biological tissue, is obtained using an image acquisition device. An image processor implements a moving window having a j·k·l size. In the moving window, j is a number of wavelengths, also equal to the number of images in the set, k is a number of pixels of the window in a first dimension of the images of the biological tissue (for example, along a horizontal width of the biological tissue forming a pixel row), and l is a number of pixels of the window in a second dimension of the images of the biological tissue (for example, along a vertical height of the biological tissue forming a pixel column). In a particular embodiment, l may be equal to one (1) pixel in which case the moving window forms a two-dimensional matrix defined by a number of wavelengths and a pixel width of the moving window. The texture analysis using GLOM and/or GLRLM and/or MRFM is performed using information contained in this window at an initial position. A value of a specific texture feature is calculated based on a level of energy, a level of correlation, a level of contrast or a level of homogeneity in the GLOM or GLRLM or MRFM matrix. This value becomes the value of a first pixel of the texture image and thus characterizes the texture. The window is then moved by a predetermined number of pixels, for example one or more pixels, in space along the first dimension (for example horizontally) on the set of images of the biological tissue. Information of this window is again extracted and analysed to define a second pixel of the texture image. The process continues until the moving window reaches the end of the first dimension (the end of a first row) and then continues by displacing the moving window by another predetermined number of pixels, for example one or more pixels, along a second dimension (for example vertically, on another pixel row). The process goes on until the moving window has fully covered the set of images or biological tissue.

First order statistics (FOS) based on a histogram of the texture image may be calculated at operation 114. The FOS may include any one or more of intensity mean, intensity skewness, intensity variance and intensity kurtosis of the texture image. The FOS of operation 114 may result in the determination of a similarity value that can be added to the features of the biological tissue. Optionally, the statistical information obtained at operation 114 may be subject to a supervised or unsupervised dimensional reduction at operation 115, using for example one of a principal component analysis (PCA) or a discriminant analysis (DA). The statistical information, with or without dimensional reduction, is used in the following operation 116, which comprises a classification of the biological tissue based on its features and, optionally, on the similarity value. The classification may be made using any one, or more, of the various FOS found in the texture images, for example a texture reflecting a contrast, correlation, homogeneity, and/or energy. The classification may lead to a negative result 118, in which case the biological tissue is classified as normal, or to a positive result 120, in which case the biological tissue is classified as abnormal. In more details, the classification made at operation 116 may comprise a comparison between predetermined values on one hand, and statistics of the texture image on the other hand. Alternatively or in addition, the classification made at operation 116 may comprise identifying a variation between the texture image or statistics thereof and a previous texture image obtained from a biological tissue of the same subject, for example the same ROI of the subject, or statistics thereof. The classification made at operation 116 may also use FOS to characterize the variation between the texture image and the previous texture image. The variation between the texture image and the previous texture image may be identified after normalization of an intensity of the texture image and of an intensity of the previous texture image. Without limitation, the intensity of various pixels of an image may be normalized within an intensity range between 0 and 1, these values being dimensionless. A progression of the anomaly may be determined at least in part based on the variation between the texture image and the previous texture image.

Optionally, operation 122 may further use spectral information of the first, second and any further image contained in the hyperspectral image, at their respective wavelengths, to define a spectral signature of the biological tissue. The spectral signature is a vector containing information of the intensity (i.e. the luminance) of a specific pixel over available wavelengths. This vector may also represent a mean intensity value of a specific region over the available wavelengths. It becomes possible to compare the spectral signature with a reference spectral signature from a control biological tissue so that operation 116 may further classify the biological tissue of the subject as normal (negative result 118) or abnormal (positive result 120) at least in part based on this comparison. The classification of the biological tissue may therefore be supervised and based on reference information, or unsupervised.

The spectral signature may comprise pixel-by-pixel information related to the biological tissue. Alternatively, the spectral signature may be a mean spectral signature defined over the area of the biological tissue or over a part of the biological tissue. Otherwise stated, the spectral signature of the biological tissue may be determined at any level of granularity useful for the detection of an anomaly and/or for the diagnostic of a condition present in the biological tissue. A comparison of the spectral signature the biological tissue with the spectral signature from a control biological tissue or with a spectral signature obtained from the same or equivalent biological tissue of the subject at an earlier time allows to determine a percentage of differentiation of the texture image for every pixel of the biological tissue, It becomes possible to identify a variation between the spectral signature of the biological tissue and a previous spectral signature obtained from the same or equivalent biological tissue of the subject, and to determine a progression of the anomaly at least in part based on the variation between the spectral signature of the biological tissue and the previous spectral signature. The determination of the progression of the anomaly may be particularly useful in assessing the effectiveness of a treatment of the subject When the classification yields a positive result 120, the sequence 100 may continue with one or more operations useful in providing information about the anomaly found in the biological tissue to an operator or caregiver. For instance, an operation 124 may localize the anomaly within the biological tissue, operation 126 may quantify the anomaly of the biological tissue, and operation 128 may provide a visual mapping of the biological tissue for display on a computer monitor or similar display. Information provided to the operator or caregiver may be used to establish a diagnosis of the subject at least in part based on the comparison between the texture image and the reference texture image and/or on the comparison between the spectral signature of the biological tissue and the reference spectral signature. Without limitation, the present technology may be used to detect the presence of biomarkers, for example biomarkers correlated with cerebral amyloids, in an ROI of the subject. It becomes possible, for example, to detect signs of Alzheimer's disease in the retina of the subject, at least in part based on the texture analysis of operations 108 and 110 and also based on results of other operations in the sequence 100. Other illness that may become detectable using the operations of the sequence 100 include, without limitation, arteriosclerosis, diabetic retinopathy, glaucoma, age related macular degeneration, skin cancer, and prostate cancer.

Figure 4:
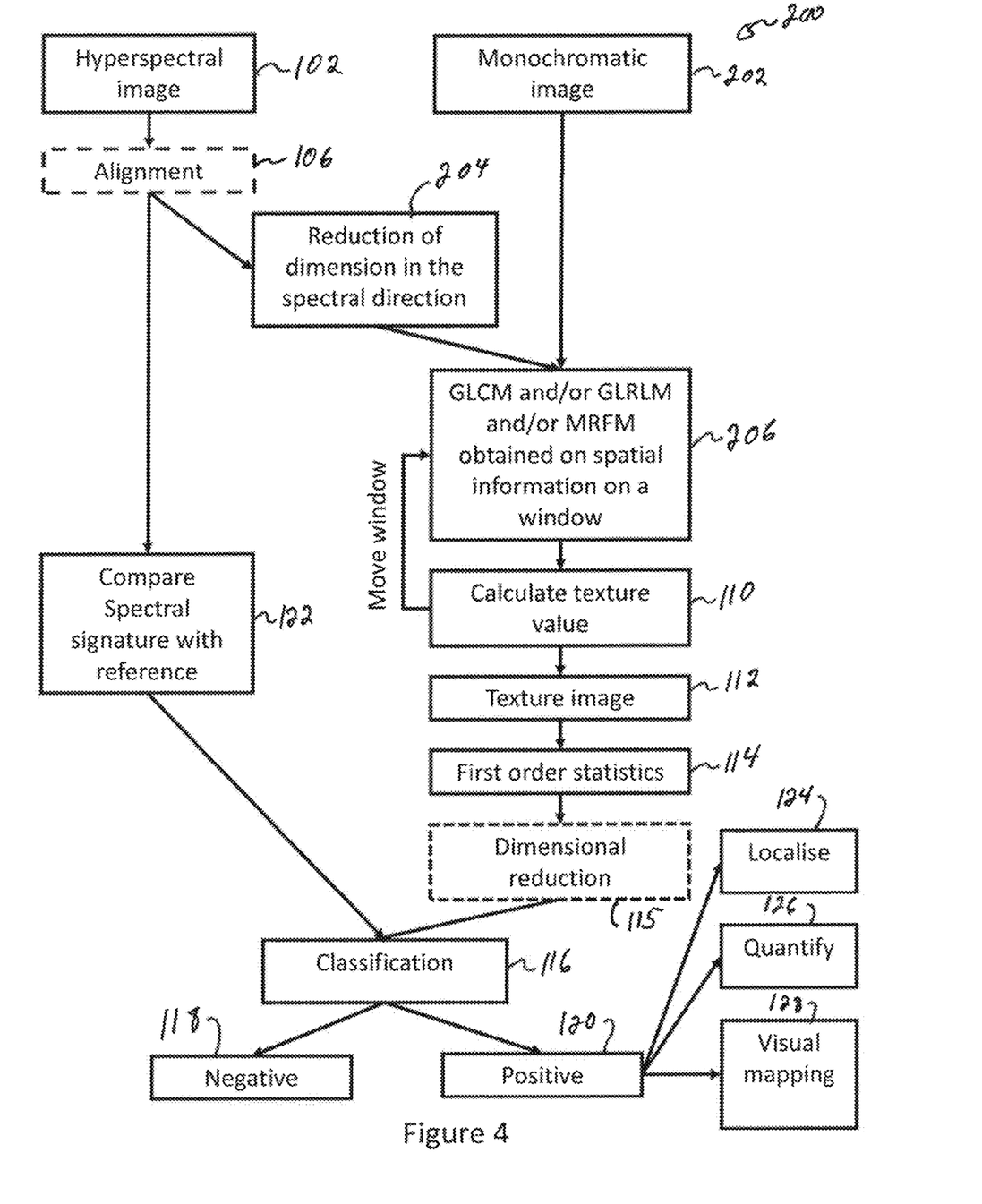
FIG. 4 is a sequence diagram of a process using GLOM and/or GLRLM and/or MRFM in spatial direction and using texture information to classify images of a biological tissue according to another embodiment.

FIG. 4 is a sequence diagram of a process using GLOM and/or GLRLM and/or MRFM in spatial direction and using texture information to classify images of a biological tissue according to another embodiment. On FIG. 4, a sequence 200 comprises a plurality of operations that may be executed in variable order, some of the operations possibly being executed concurrently, some of the operations being optional. Some of the operations in the sequence 200 are the same as, or equivalent to some operations of the sequence 100 and are identified with the same numerals for consistency. Those operations that are the same as, or equivalent to those described in relation to FIG. 3 are not described in details for brevity.

In the sequence 200, a texture analysis of the biological tissue is performed using spatial information of a monochromatic image of the biological tissue. In one variant, the monochromatic image may be obtained directly at operation 202. In another variant, a hyperspectral image may be obtained at operation 102, following which a spectral dimension of the hyperspectral image is reduced at operation 204 to provide the monochromatic image of the biological tissue. This reduction of the spectral dimension may for example be obtained by calculating a mean of corresponding pixels at a plurality of wavelengths of the hyperspectral image or through using a principal component analysis (PCA) or a discriminant analysis (DA) of the hyperspectral image.

Regardless of the manner in which the monochromatic image is obtained, a texture analysis of the biological tissue is performed using spatial information of the monochromatic image of the biological tissue. This texture analysis is performed at operations 206 and 110. For each pixel of the first, second and any further image of the biological tissue, the texture analysis is performed at operation 108 using gray level co-occurrence matrix (GLCM), gray level run length matrix (GLRLM), Markov Random Field Matrix (MRFM) or any combination of GLCM, GLRLM and MRFM applied on spatial information of the monochromatic image of the biological tissue. A texture value is calculated at operation 110. Operations 206 and 110 are repeated over pixel rows and pixel columns of the monochromatic image.

Generation of a texture image at operation 112, FOS calculation at operation 114, dimensional reduction made at operation 115, classification of the biological tissue at operation 116, determination of the results 118 or 120 and presentation of the results at operations 124, 126 and/or 128 are essentially the same as in the foregoing description of FIG. 3, although based on the monochromatic image, and the results and information obtained from the sequence 200 may be used for the same diagnosis purposes as those of sequence 100.

In a non-limiting embodiment, a set of biological tissue images, including first, second and any further images of the biological tissue, is obtained using an image acquisition device. An image processor implements a moving window having a k·l size. In the moving window, k is a number of pixels of the window in a first dimension of the images of the biological tissue (for example, along a horizontal width of the biological tissue forming a pixel row), while l is a number of pixels of the window in a second dimension of the images of the biological tissue (for example, along a vertical height of the biological tissue). The texture analysis using GLOM and/or GLRLM and/or MRFM is performed using information contained in this window at an initial position. A value of a specific texture feature (contrast, energy, correlation or homogeneity) is calculated. This value becomes the value of a first pixel of the texture image and thus characterizes the texture. The window is then moved by a predetermined number of pixels, for example one or more pixels, in space along the first dimension (for example horizontally) on the set of images of the biological tissue. Information of this window is again extracted and analysed to define a second pixel of the texture image. The process continues until the moving window reaches the end of the first dimension (the end of a first row) and then continues by displacing the moving window by another predetermined number of pixels, for example one or more pixels, along the second dimension (for example vertically, on another pixel row). The process goes on until the moving window has fully covered the set of images or biological tissue.

Optionally in the context of the sequence 200, images at various wavelengths contained in the hyperspectral image obtained at operation 102 may be subject to an alignment registration at operation 106, if needed to overcome alignment imperfections caused by an imaging device supplying the hyperspectral image. Thereafter, operation 122 may use spectral information contained in the hyperspectral image to define a spectral signature of the biological tissue in order to then compare the spectral signature with a reference spectral signature. Then, operation 116 may further classify the biological tissue of the subject as normal or abnormal based at least in part on a comparison between the spectral signature and the reference spectral signature.

In the sequences 100 and 200, each of the operations 102 to 128 and/or 202 to 206 may be configured to be processed by one or more processors, the one or more processors being coupled to a memory.

Figure 5:
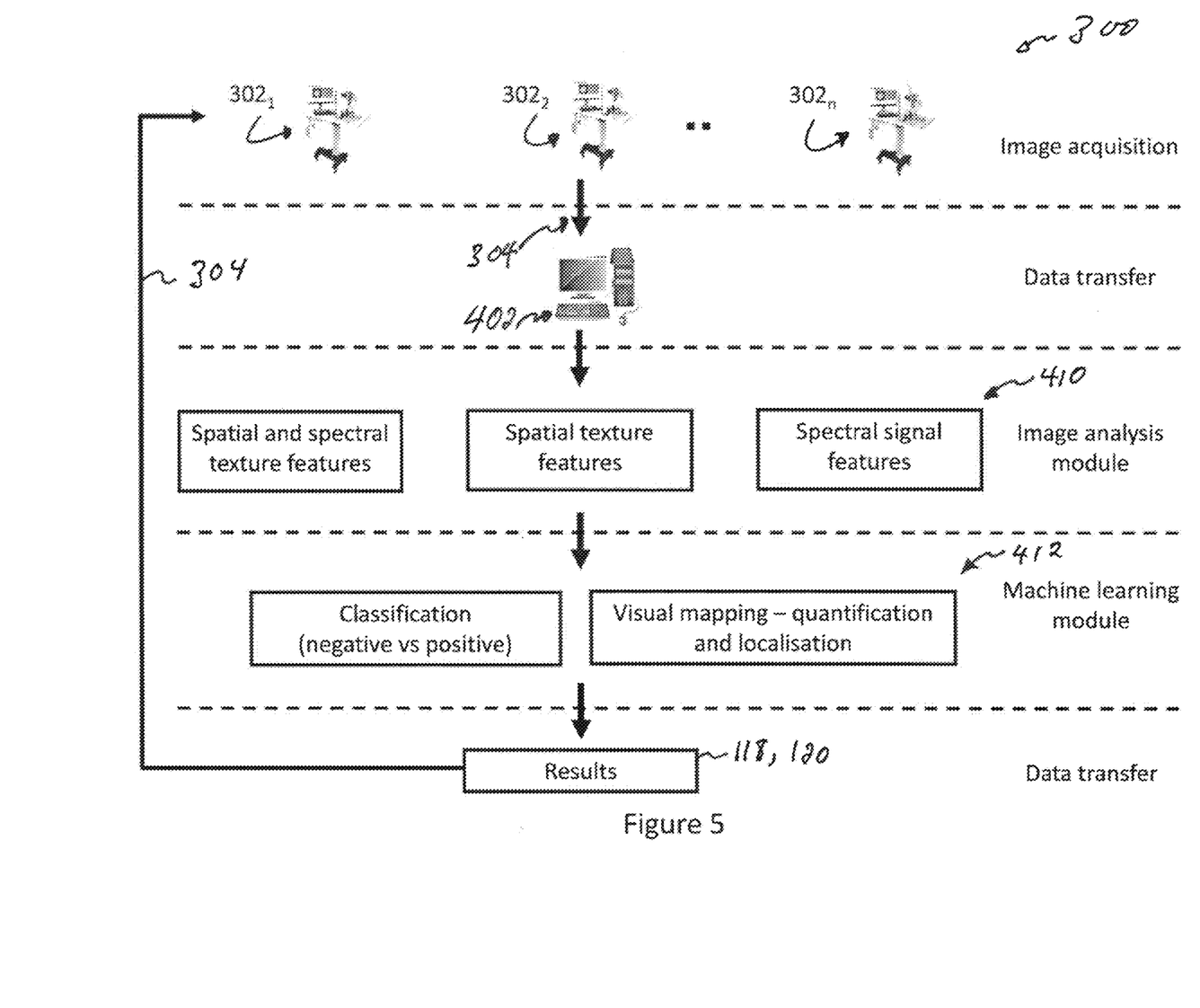
FIG. 5 is a high-level network diagram showing elements of a system for classifying images of the biological tissue.
Figure 6:
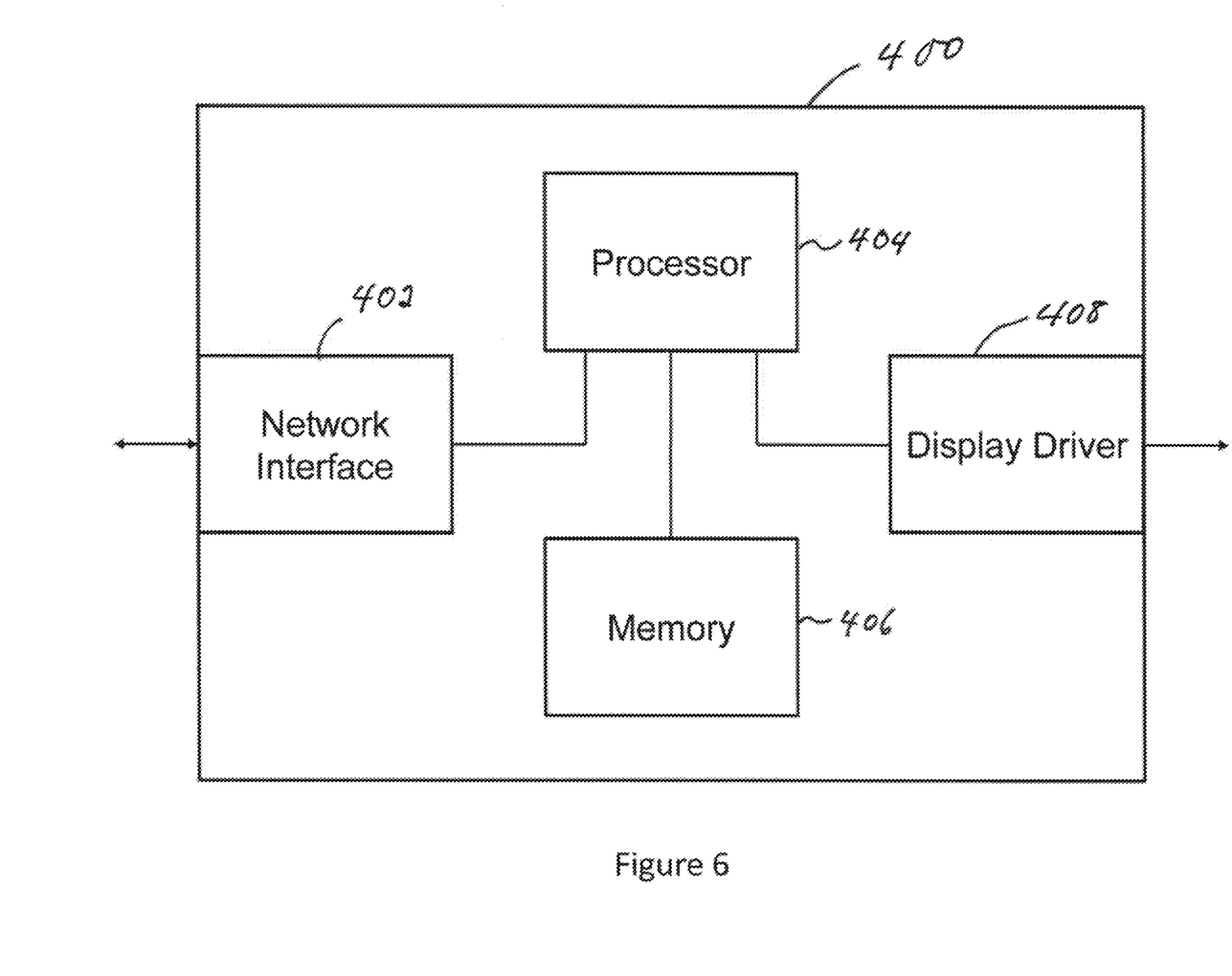
FIG. 6 is a block diagram of a device for classifying images of the biological tissue.

FIG. 5 is a high-level network diagram showing elements of a system for classifying images of the biological tissue. FIG. 6 is a block diagram of a device for classifying images of the biological tissue. Considering at once FIGS. 5 and 6, a network 300 includes device 400 for classifying images of the biological tissue. The network 300 may comprise one client device $302_1$ or a plurality of client devices such as $302_1$, $302_2$ ... $302_n$. Each client device 302 comprises an image acquisition device (not specifically shown), for example a camera, a plurality of monochromatic images and/or an hyperspectral image of an ROI of a subject. The client devices $302_1$, $302_2$ ... $302_n$ use a data transfer connection 304 to forward images of biological tissues from their image acquisition devices to the device 400. In turn, the device 400 comprises a network interface 402, a processor 404 and may further comprises a memory 406 and a display driver 408. The processor 404 implements an image analysis module 410 and a machine learning module 412. The device 400 outputs, for a given biological tissue, one of the negative result 118 or positive result 120 that can be transmitted via the data transfer connection 304 towards the client device 302 having submitted images of the given biological tissue. The data transfer connection 304 may comprise, without limitation, the Internet, a cloud network interface, a private network interface, a local area network, a virtual provide network, and the like. The data transfer connection 304 may, without limitation, be realized over one or more wired connection such as optical cables or copper cables, one or more wireless connections, or any combination thereof.

In more details, the network interface 402 of the device 400 acts as a receiver of a hyperspectral image containing at least a first image and a second image of the biological tissue, or as a receiver of a monochromatic image of the biological tissue.

In the case where the device 400 receives an hyperspectral image, the processor 404 may perform an alignment registration of the first and second images and any further image contained therein to align corresponding pixels of the first, second and any further images that correspond to a same element of the biological tissue. If necessary, the processor 404 may calibrate intensities of the first, second and any further images.

In one variant, the processor 404 is configured to perform a texture analysis of the biological tissue using spatial information of the first and second images and to resolve the texture analysis over a first wavelength of the first image and over a second wavelength of the second image. In the same or another variant, the processor 404 is configured to perform a texture analysis of the biological tissue using spatial information of the monochromatic image of the biological tissue. In either cases, the processor 404 may use a GLOM and/or a GLRLM and/or a MRFM technique to perform the texture analysis. The processor 404 may generate a texture image based on the texture analysis of either the first and second images or the monochromatic image. The processor 404 may then classify the biological tissue of the subject as normal or abnormal at least in part based on a comparison between first order statistics of the texture image and predetermined values. The processor 404 may also to localise the anomaly within the biological tissue and/or quantify the anomaly. The processor 404 may cause a display (not shown) connected to the display driver 408 to display the texture image. The processor 404 may also cause the network interface 402 to transmit one or more of the texture image, a classification of the biological tissue, a quantification of a variation from the reference image to the client device having supplied the image or images of the biological tissue.

The memory 406 may store information elements such as statistical information related to anomalies found in the biological tissue, a reference texture image of the biological tissue, a previous texture image obtained from the biological tissue of the same subject, and any combination thereof. The processor 404 may use this information from the memory 406 in the classification of the biological tissue.

In addition to the features mentioned in the description of FIGS. 5 and 6, the device 400 may further be adapted to execute any one of the functions and operations described in the foregoing description of FIGS. 4 and 5, including any combination of these operations.

Figure 7:
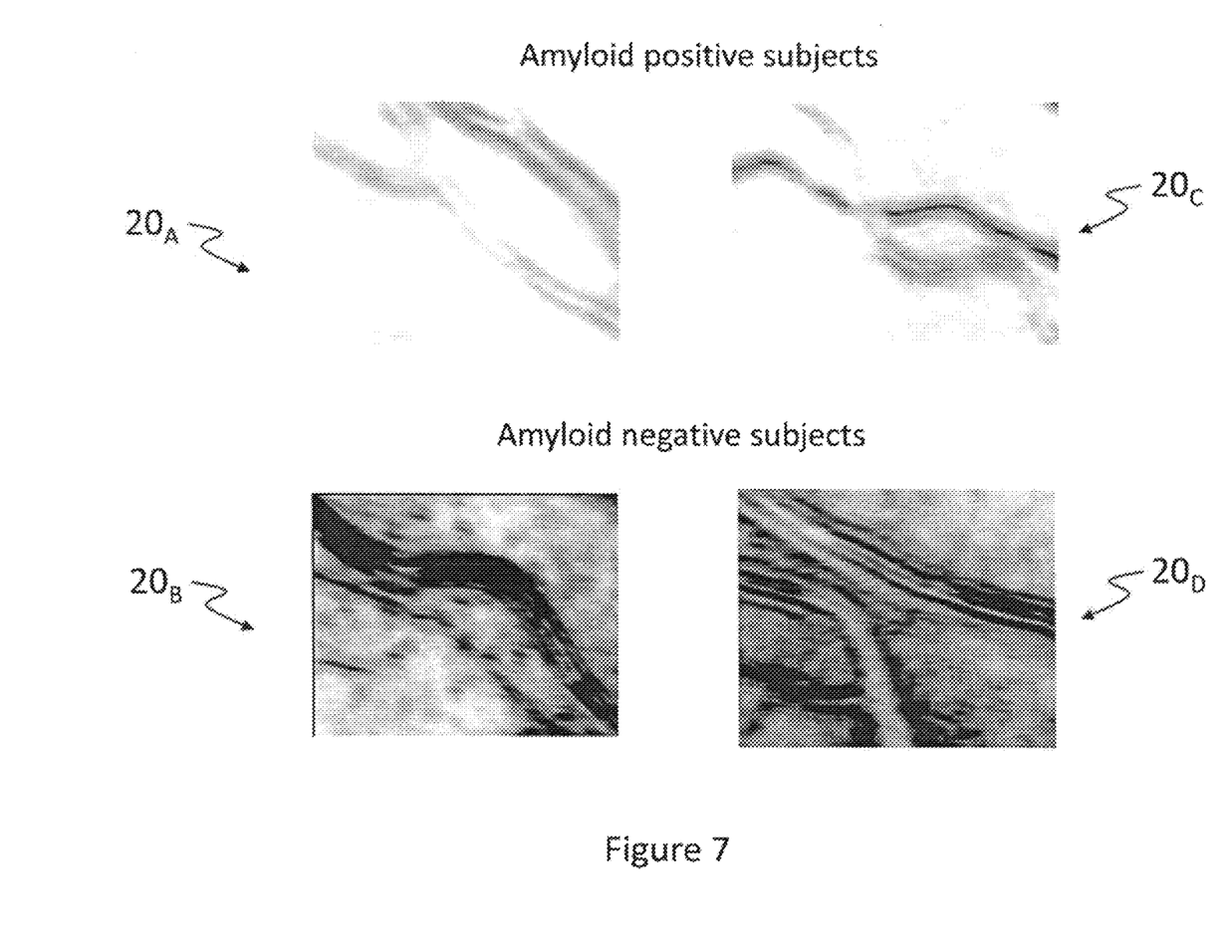
FIG. 7 is a representation of texture correlations based on spatial and spectral GLOM for regions of interest of four subjects, two of which being amyloid positive.

FIG. 7 is a representation of texture correlations based on spatial and spectral GLCM for regions of interest of four subjects, two of which being amyloid positive. Four (4) photographs were obtained using the techniques described hereinabove, two (2) of these photographs being obtained for the same patients "A" and "B", introduced in the foregoing description of FIG. 1.

Photograph $20_A$ shows the biological tissue for the amyloid positive patient "A" while photograph $20_B$ shows the biological tissue for the amyloid negative "patient B"—photograph $20_B$ is actually introduced in the foregoing description of FIG. 2. Comparing photographs $10_A$ and $20_A$, and comparing photographs $10_B$ and $20_B$, the improvement in terms of contrast and readability of these images is striking. Photographs $20_C$ and $20_D$ were obtained for two (2) other subjects, patients "C" and "D"; in particular photograph $20_C$ represents a similar biological tissue for another amyloid positive subject while photograph $20_D$ represents a similar biological tissue for another amyloid negative subject. Once again, considering photographs $20_C$ and $20_D$, the techniques disclosed herein provide medical images that have much improved readability when compared to those obtained using earlier techniques.

Figure 8:
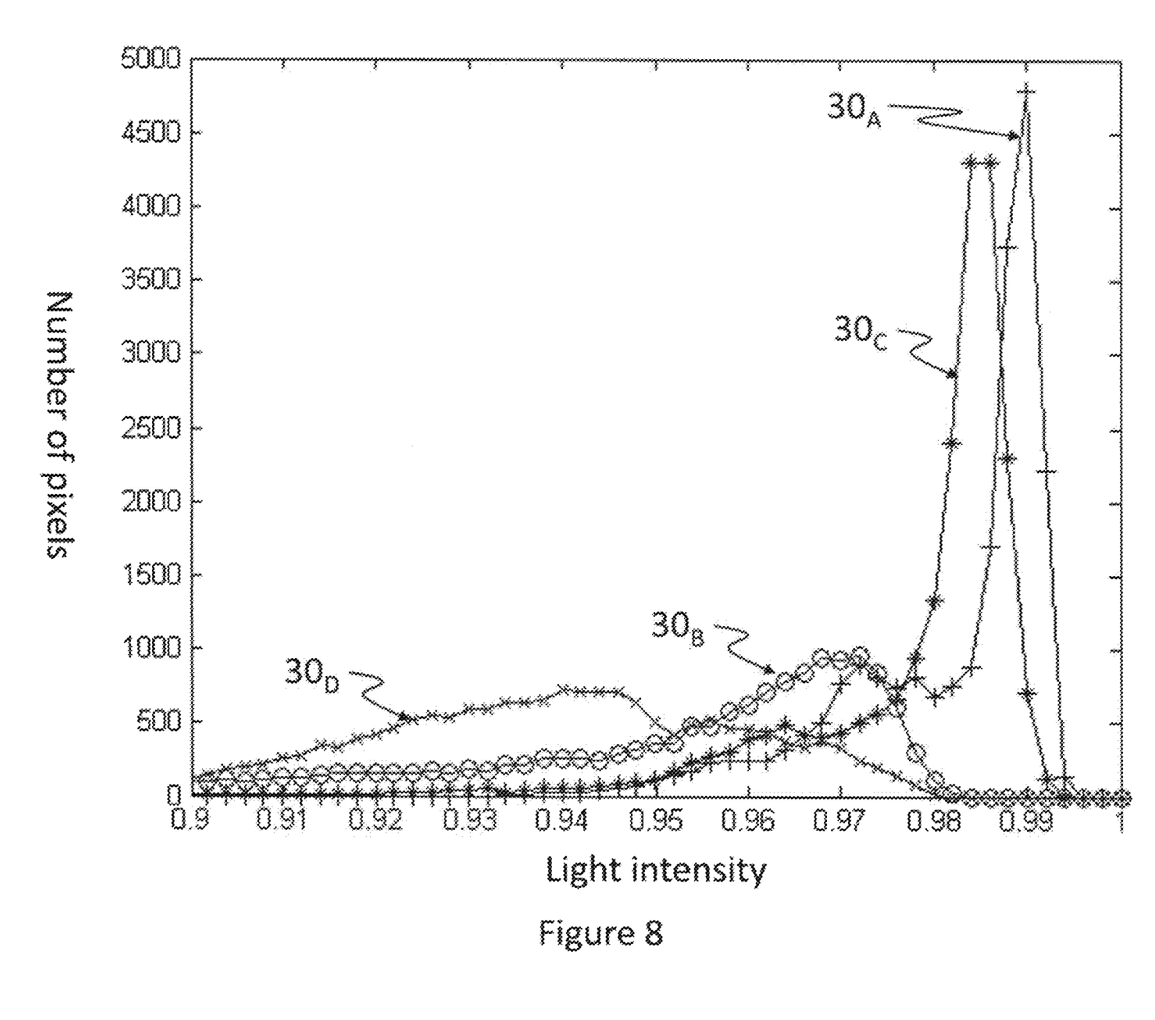
FIG. 8 is a histogram of correlation texture-images based on spatial and spectral GLOM for regions of interest of the four subjects of FIG. 7.

FIG. 8 is a histogram of correlation texture-images based on spatial and spectral GLCM for regions of interest of the four subjects of FIG. 7. Curves $30_A$, $30_C$, $30_B$ and $30_D$ show that pixel intensity reaches high peaks for large numbers of pixels in the cases of the two (2) amyloid positive patients "A" and "C", such peaks being absent in the case of the two (2) amyloid negative patients "B" and "D".

Figure 9:
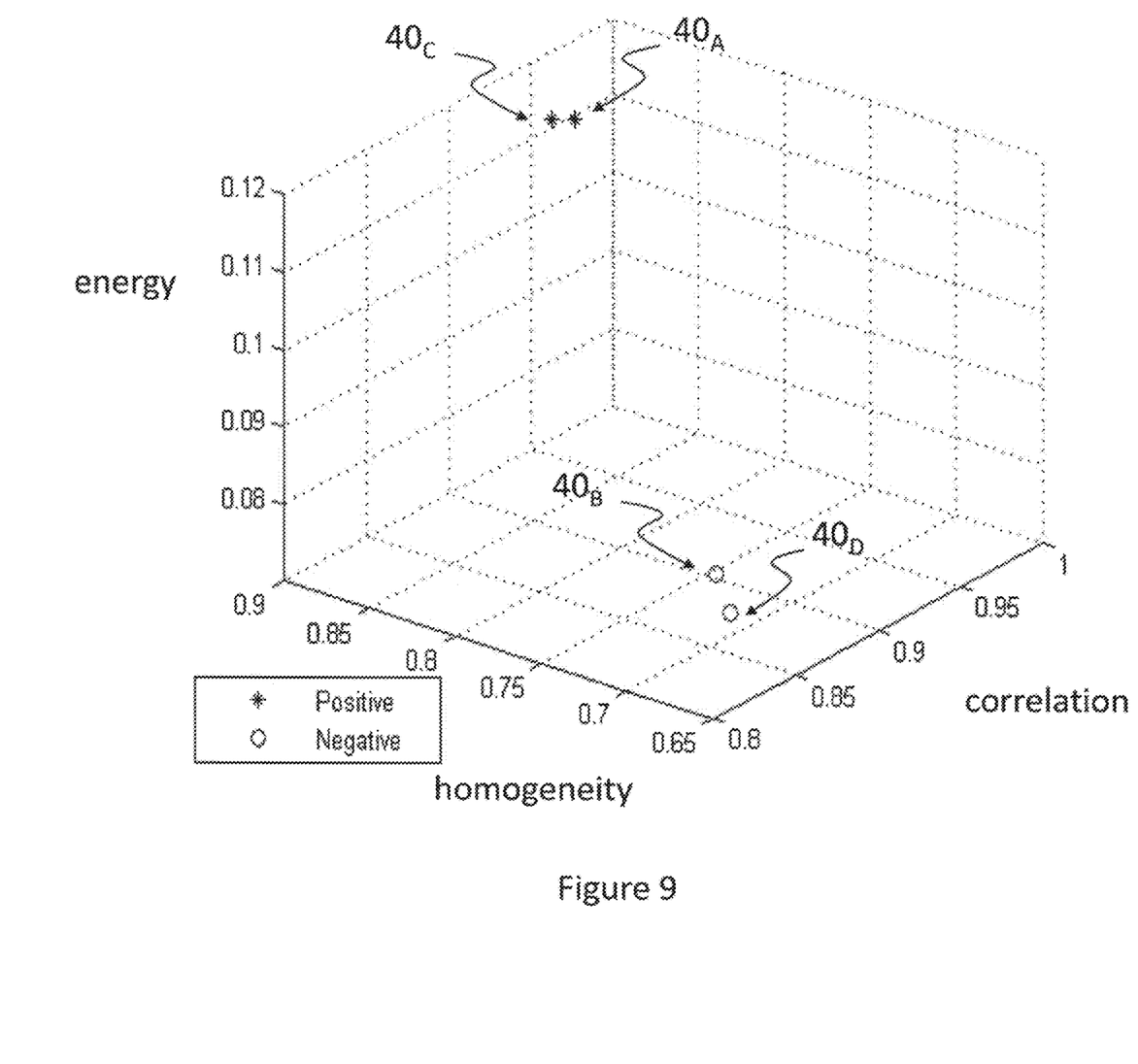
FIG. 9 is a three-dimensional representation of a statistical classification based on spatial and spectral GLOM for the four subjects of FIG. 7.

FIG. 9 is a three-dimensional representation of a statistical classification based on spatial and spectral GLCM for the four subjects of FIG. 7. Results of a first order statistics (FOS) calculation based on the mean value of the homogeneity image, correlation image and energy image based on spatial GLCM are shown on the graph of FIG. 9, wherein three (3) axes provide mean correlation, mean homogeneity and mean energy of images formed of reflectance emissions from biological tissues of these patients. The amyloid positive patients "A" and "C" are represented by corresponding points $40_A$ and $40_C$ in the 3D space of FIG. 9 while the amyloid negative patients "B" and "D" are represented by corresponding points $40_B$ and $40_D$. A very clear distinction appears between the positions of amyloid negative or positive patients within the 3D space, demonstrating the effectiveness of the procedure of FIG. 4 in detecting anomalies within biological tissues of those patients. FIG. 9 shows mean values for the correlation, homogeneity and energy of the biological tissue images. Though not illustrated, it is possible to build similar graphs showing the kurtosis, the skewness or the variance of the contrast, correlation, homogeneity and energy of the biological tissue images.

Figure 10:
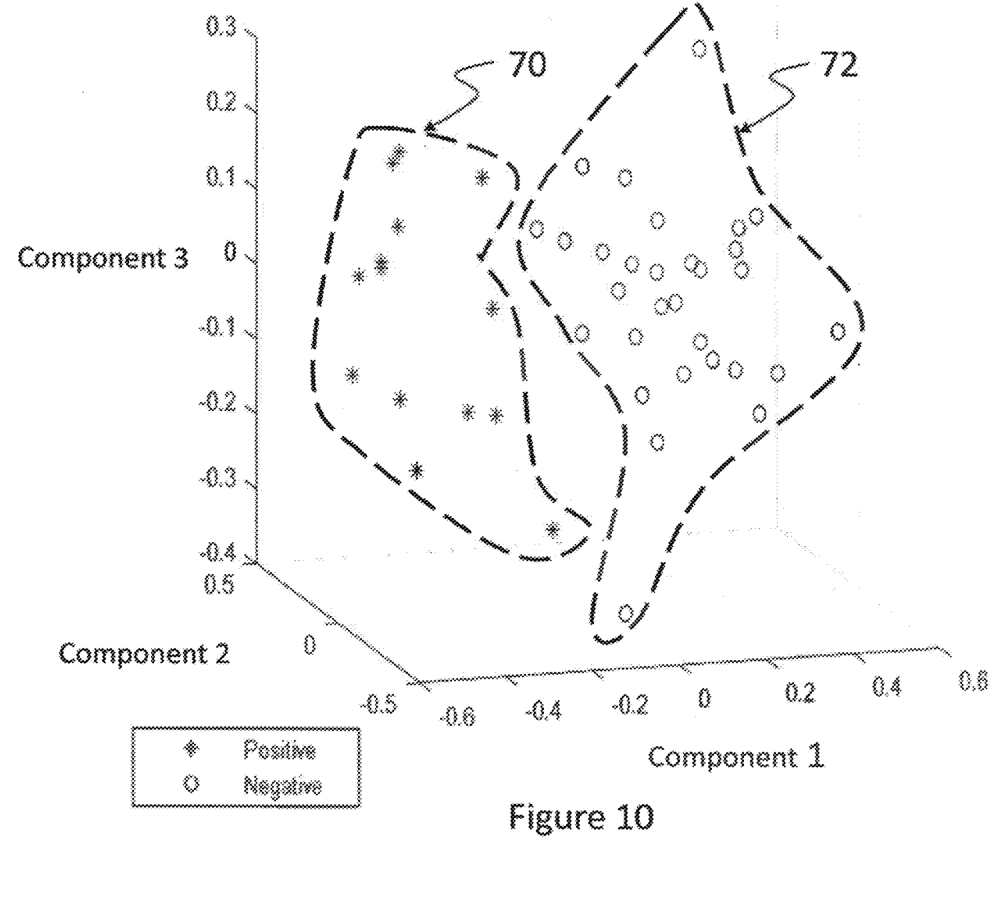
FIG. 10 is another three-dimensional representation of a statistical classification based on spatial and spectral GLOM for a larger number of subjects, the data being obtained following dimensional reduction of the statistical classification.

Referring again to FIGS. 3 and 4, optionally, a dimensional reduction operation 115 may be applied on the statistical information obtained at operation 114, before classification of the biological tissue at operation 116. FIG. 10 is another three-dimensional representation of a statistical classification based on spatial and spectral GLCM for a larger number of subjects, the data being obtained following dimensional reduction of the statistical classification. Comparing the graph of FIG. 10 with the graph of FIG. 9, a larger number of subjects is used to produce a first cloud 70 of positive results and a second cloud 72 of negative results. The results are obtained following a selection of three (3) most important components of a discriminant analysis (DA) at operation 115.

Those of ordinary skill in the art will realize that the description of the method and system for detecting an anomaly within a biological tissue are illustrative only and are not intended to be in any way limiting. Other embodiments will readily suggest themselves to such persons with ordinary skill in the art having the benefit of the present disclosure. Furthermore, the disclosed method and system may be customized to offer valuable solutions to existing needs and problems related to the limited adaptability of current imaging techniques and to the inherent ambiguity of images obtained using such techniques. In the interest of clarity, not all of the routine features of the implementations of method and system are shown and described. In particular, combinations of features are not limited to those presented in the foregoing description and combinations of elements listed in the appended claims form an integral part of the present disclosure. It will, of course, be appreciated that in the development of any such actual implementation of the method and system, numerous implementation-specific decisions may need to be made in order to achieve the developer's specific goals, such as compliance with application-, system-, and business-related constraints, and that these specific goals will vary from one implementation to another and from one developer to another. Moreover, it will be appreciated that a development effort might be complex and time-consuming, but would nevertheless be a routine undertaking of engineering for those of ordinary skill in the field of medical imaging having the benefit of the present disclosure.

In accordance with the present disclosure, the components, process operations, and/or data structures described herein may be implemented using various types of operating systems, computing platforms, network devices, computer programs, and/or general purpose machines. In addition, those of ordinary skill in the art will recognize that devices of a less general purpose nature, such as hardwired devices, field programmable gate arrays (FPGAs), application specific integrated circuits (ASICs), or the like, may also be used. Where a method comprising a series of operations is implemented by a computer or a machine and those operations may be stored as a series of instructions readable by the machine, they may be stored on a tangible medium.

Systems and modules described herein may comprise software, firmware, hardware, or any combination(s) of software, firmware, or hardware suitable for the purposes described herein. Software and other modules may reside on servers, workstations, personal computers, computerized tablets, personal digital assistants (PDA), and other devices suitable for the purposes described herein. Software and other modules may be accessible via local memory, via a network, via a browser or other application or via other means suitable for the purposes described herein. Data structures described herein may comprise computer files, variables, programming arrays, programming structures, or any electronic information storage schemes or methods, or any combinations thereof, suitable for the purposes described herein.

The present disclosure has been described in the foregoing specification by means of non-restrictive illustrative embodiments provided as examples. These illustrative embodiments may be modified at will. The scope of the claims should not be limited by the embodiments set forth in the examples, but should be given the broadest interpretation consistent with the description as a whole.

What is claimed is:

1. A method for imaging a biological tissue, comprising:
   obtaining a monochromatic image of the biological tissue;
   performing a texture analysis of the biological tissue using spatial information of the monochromatic image of the biological tissue to identity features of the biological tissue;
   generating a texture image based on the features of the biological tissue by:
      defining a moving window having a k·l size, wherein k is a number of pixels of the moving window defined in a first dimension of the image of the biological tissue and wherein l is a number of pixels of the moving window defined in a second dimension of the image of the biological tissue,
      using information from the image of the biological tissue contained in the moving window to calculate a value of a pixel of the texture image,
      successively displacing the moving window by a first predetermined number of pixels in the first dimension of the image of the biological tissue,
      repeating the calculation of pixel values of the texture image following each displacement of the moving window in the first dimension of the image of the biological tissue,
      successively displacing the moving window by a second predetermined number of pixels in the second dimension of the image of the biological tissue, and
      repeating the calculations of pixel values of the texture image and the displacements of the moving window over the first dimension of the image of the biological tissue following each displacement of the moving window over the second dimension of the image of the biological tissue; and
   classifying the biological tissue of the subject as normal or abnormal at least in part based on a comparison between first order statistics of the texture image and predetermined values.

2. The method of claim 1, further comprising performing a dimensional reduction of the first order statistics in view of classifying the biological tissue of the subject as normal or abnormal.

3. The method of claim 1, further comprising:
   acquiring a hyperspectral image of the biological tissue; and
   reducing a spectral dimension of the hyperspectral image to provide the monochromatic image of the biological tissue.

4. The method of claim 1, further comprising:
   acquiring a hyperspectral image of the biological tissue; and
   defining a spectral signature of the biological tissue using spectral information of the hyperspectral image;
   wherein classifying the biological tissue of the subject as normal or abnormal is further based at least in part on a comparison between the spectral signature of the biological tissue and a reference spectral signature.

5. A system for imaging a biological tissue, comprising:
   a receiver of a monochromatic image of the biological tissue; and
   a processor operatively connected to the receiver, the processor being configured to:

perform a texture analysis of the biological tissue using spatial information of the monochromatic image of the biological tissue to identity features of the biological tissue;

generate a texture image based on the features of the biological tissue by:
- defining a moving window having a k·l size, wherein k is a number of pixels of the moving window defined in a first dimension of the image of the biological tissue and wherein l is a number of pixels of the moving window defined in a second dimension of the image of the biological tissue,
- using information from the image of the biological tissue contained in the moving window to calculate a value of a pixel of the texture image,
- successively displacing the moving window by a first predetermined number of pixels in the first dimension of the image of the biological tissue,
- repeating the calculation of pixel values of the texture image following each displacement of the moving window in the first dimension of the image of the biological tissue,
- successively displacing the moving window by a second predetermined number of pixels in the second dimension of the image of the biological tissue, and
- repeating the calculations of pixel values of the texture image and the displacements of the moving window over the first dimension of the image of the biological tissue following each displacement of the moving window over the second dimension of the image of the biological tissue; and classify the biological tissue of the subject as normal or abnormal at least in part based on a comparison between first order statistics of the texture image and predetermined values.

6. The system of claim 5, wherein the processor is further configured to perform a dimensional reduction of the first order statistics in view of classifying the biological tissue of the subject as normal or abnormal.

7. The system of claim 5, wherein the processor is further configured to localise an anomaly within the biological tissue.

8. The system of claim 5, wherein the processor is further configured to quantify an anomaly within the biological tissue.

9. The system of claim 5, further comprising a display driver, wherein the processor is further configured to cause a display connected to the display driver to display the texture image.

10. The system of claim 5, further comprising a memory operatively connected to the processor, the memory storing information elements selected from statistical information related to anomalies found in the biological tissue, a reference texture image of the biological tissue, a previous texture image obtained from the biological tissue and a combination thereof.

11. The system of claim 5, wherein the receiver is part of a network interface adapted to receive the monochromatic image of the biological tissue from a client terminal and to transmit, to the client terminal, an element selected from the texture image, a classification of the biological tissue, a quantification of a variation between the texture image and a reference texture image, and a combination thereof.

12. The system of claim 11, further comprising an image acquisition device operatively connected to the network interface, the image acquisition device being adapted to acquire a plurality of pixel rows and a plurality of pixel columns of the monochromatic image of the biological tissue.

* * * * *